United States Patent [19]

Peat

[11] 4,439,432

[45] Mar. 27, 1984

[54] TREATMENT OF PROGESTERONE DEFICIENCY AND RELATED CONDITIONS WITH A STABLE COMPOSITION OF PROGESTERONE AND TOCOPHEROLS

[76] Inventor: Raymond F. Peat, 300½ N. Jefferson St., Eugene, Oreg. 97402

[21] Appl. No.: 360,587

[22] Filed: Mar. 22, 1982

[51] Int. Cl.³ .............................................. A61K 31/56
[52] U.S. Cl. .................................................... 424/240
[58] Field of Search ................................ 424/240, 284

[56] References Cited

PUBLICATIONS

Chemical Abstracts (1974), vol. 80, Par. 124760u.

Primary Examiner—Elbert L. Roberts
Attorney, Agent, or Firm—Ellen P. Winner

[57] ABSTRACT

This invention relates to the composition of a biologically compatible high concentration solution of progesterone, which is stable and non-toxic, and which can be used transdermally, orally, and in suppository and pessary form for the correction of progesterone deficiency states and other diseases.

10 Claims, No Drawings

TREATMENT OF PROGESTERONE DEFICIENCY AND RELATED CONDITIONS WITH A STABLE COMPOSITION OF PROGESTERONE AND TOCOPHEROLS

The present invention relates to the composition of a biologically compatible high concentration solution of progesterone in tocopherol, with or without modifying substances, which can be used transdermally, orally, and in suppository and pessary form, for the correction of progesterone deficiency states and other diseases.

Progesterone deficiency can be defined in relation to a norm, and also in relative terms, taking into account the absolute level of progesterone in the tissues and the presence and levels of antagonists to its actions, including estrogens, prolactin, and androgenic steroids, and it can also be defined in the empirical sense, in which symptoms abate when progesterone is administered.

Physicians have long sought an oral and/or transdermal form of progesterone which is stable in high concentration and which is assimilated easily by the body, for use when injectable forms of progesterone are not tolerated. A non-toxic and low-allergenic form is of special value for use in allergic patients, and for all users the absence of a toxic solvent is of obvious value.

Many physicians have used progesterone dissolved in ethanol, but ethanol has a higher mutual solubility with water than with progesterone, causing the bulk of the progesterone to be crystallized out of solution as the alcohol solvent mixes with biological fluids. That composition is ineffective because it fails to deliver progesterone in practical quantities and usable form. Other compositions containing solvents such as benzyl benzoate, benzoyl alcohol or phenol are limited in their applicability because of their toxicity, irritating properties, or allergenicity. Since allergies are common in the condition of progesterone deficiency, it follows that the effectiveness of compositions containing allergenic solvents is limited.

Progesterone has been used medically to treat pregnancy complications, menstrual abnormalities, menopausal difficulties, several types of malignant and non-malignant tumors, neurological and psychological symptoms, and many other specific problems. The composition described in this patent can be used effectively for all of the purposes for which progesterone in its older compositions is effective. In addition, the composition described in this patent is useful for several new purposes, including treatment of psoriasis, eczema, senile skin changes including warts, superficial burns, allergies, abnormal hair growth resulting from androgen excess, intestinal inflammation and bowel spasms, migraine, and for promoting maturation of thymus-derived lymphocytes, and as a contraceptive.

It is an object of the present invention to provide a composition and method for the treatment of progesterone deficiency conditions.

It is another object of the present invention to provide such a composition and method which overcome the shortcomings of the prior art.

It is another object of the present invention to provide a composition which does not decompose into solvent and crystallized solute, progesterone, under any presently known conditions of storage or use.

It is another object of the present invention to provide such a composition which is non-toxic and which may be used frequently over long periods without adversely affecting the tissues which it contacts.

It is a further object of the present invention to provide such a composition which is economical and easily used for the prevention and treatment of progesterone deficiency conditions and other diseases.

Still further objects and the entire scope of applicability of the present invention will become apparent from the detailed description and specific examples, but it should be understood that the examples, while indicating preferred embodiments of the invention, are given only for illustration, since changes within the spirit and scope of the invention will become apparent to those skilled in the art from this description.

It has been found that the above objects may be attained by a composition which contains as essential ingredients progesterone and tocopherol. As will be hereinafter explained more fully, the composition may also contain additives for various purposes. The composition may be administered by spreading on the skin, by holding in contact with mucous membranes, or by ingesting, and can be used as frequently as needed.

Suitable forms of tocopherol include d-alpha tocopherol, and mixed tocopherols of the dextro-rotatory form.

Suitable additives include coconut oil, palm kernel oil, jojoba oil, and olive lil, used in concentrations up to about 15% to lower the viscosity of the solution and to thus speed absorption; ascorbyl palmitate and/or glyceryl monophosphate in concentrations sufficient to emulsify the composition with water; biological or organic gels including aloe gel and extracts from marine algae to thicken the consistency and to stabilize the emulsion; and ethanol, in a concentration of up to about 7% by volume, to modify consistency and to increase absorption of progesterone.

The composition is prepared by mixing the ingredients to obtain a homogeneous product. Stirring at room temperature is adequate, but may require several days to reach complete homogeneity. An oxygen-free atmosphere is preferred but not essential. If higher temperatures are used for faster mixing, an oxygen-free atmosphere becomes more important to prevent oxidation of the materials.

Progesterone and tocopherol can be mixed in the proportions of from 1% to about 25% progesterone by weight, to about 75% to 99% of tocopherol, with a preferred concentration for most uses of from about 10% to 20% progesterone to about 80% to 90% tocopherol.

This invention is further described in the following specific examples, which are to be considered only as illustrative of preferred embodiments of the present invention.

EXAMPLE 1

Ten kilograms of progesterone is added to 90 kilograms of mixed tocopherols of the dextro-rotatory form, and stirred at a temperature of 45° C. until homogeneous. Thirty-five kilograms of glyceryl-monostearate is added to the composition and stirred at 45° C. until a homogeneous mixture is produced. This oil phase is then homogenized at 45° C. with a water phase composed of 200 kilograms of water mixed homogeneously with 5 kilograms of dry aloe gel, and one kilogram of sorbic acid as a preservative.

The resulting emulsion is then applied to the skin in treating systemic progesterone deficiency, and for treating local skin conditions including psoriasis, or applied to a vaginal diaphragm or pessary or inserted vaginally with an appropriate applicator, for use as a contraceptive or for treating systemic progesterone deficiency.

EXAMPLE 2

Twenty kilograms of progesterone is added to 80 kilograms of mixed tocopherols, and stirred at a temperature of 40° C. until homogeneous.

The resulting composition is applied to a pessary for use as a contraceptive, or as a local treatment for dysplasia of the uterine cervix, or is administered orally for treatment of a systemic progesterone deficiency. No preservative is needed in this composition.

EXAMPLE 3

Ten kilograms of progesterone is added to 90 kilograms of d-alpha tocopherol and stirred at a temperature of 30° C. until homogeneous.

The resulting composition is then encapsulated and administered orally for treatment of systemic progesterone deficiency.

What is claimed is:

1. A composition consisting essentially of progesterone solubilized in tocopherol.

2. A pharmaceutical composition suitable for administering progesterone to a patient in need thereof, comprising a pharmaceutically effective amount of progesterone solubilized in tocopherol.

3. The composition of claim 2 wherein progesterone is present at a concentration of from about 1% to about 25% by weight.

4. The composition of claim 2 also containing an emulsifier, water and a preservative.

5. A method for administering progesterone to a patient in need thereof comprising administering to said patient by means other than intravenous injection, a pharmaceutically effective mixture of progesterone solubilized in tocopherol.

6. The method of claim 5 which comprises the oral administration of said mixture.

7. The method of claim 5 which comprises the topical administration of said mixture.

8. The method of claim 5 which comprises placing said mixture in contact with the mucous membranes of the patient.

9. The method of contraception in which a pharmaceutically effective amount of progesterone solubilized in tocopherol is applied to the vaginal membranes and the uterine cervix by means of a vaginal diaphragm, a pessary, or other means of vaginal application in which the composition is retained within the vagina for about four hours or more after each application.

10. A method for making a pharmaceutically effective composition for the administration of progesterone to a patient in need thereof comprising solubilizing progesterone in tocopherol.

* * * * *